(12) United States Patent
Olbrich et al.

(10) Patent No.: US 7,135,328 B2
(45) Date of Patent: Nov. 14, 2006

(54) PROCESS FOR THE ENANTIOSELECTIVE REDUCTION OF 8-CHLORO-6-OXO-OCTANOIC ACID ALKYL ESTERS

(75) Inventors: Matthias Olbrich, Reichenberg (DE); Rainer Gewald, Dresden (DE)

(73) Assignee: Viatris GmbH & Co. KG, Frankfurt am Main (DE)

( * ) Notice: Subject to any disclaimer, the term of this patent is extended or adjusted under 35 U.S.C. 154(b) by 491 days.

(21) Appl. No.: 10/343,029

(22) PCT Filed: Jul. 20, 2001

(86) PCT No.: PCT/EP01/08421

§ 371 (c)(1), (2), (4) Date: Jan. 27, 2003

(87) PCT Pub. No.: WO02/10422

PCT Pub. Date: Feb. 7, 2002

(65) Prior Publication Data

US 2003/0180896 A1    Sep. 25, 2003

(30) Foreign Application Priority Data

Jul. 27, 2000 (DE) ................. 100 36 515
Nov. 11, 2000 (DE) ................. 100 56 025

(51) Int. Cl.
C12P 7/42 (2006.01)
C12P 41/00 (2006.01)
C12R 1/645 (2006.01)

(52) U.S. Cl. ....................... 435/280; 435/130
(58) Field of Classification Search ............... None
See application file for complete search history.

(56) References Cited

FOREIGN PATENT DOCUMENTS

| DE | 40 37 440 | 7/1977 |
| DE | 195 33 881 | 3/1997 |
| EP | 0 939 132 | 9/1999 |

OTHER PUBLICATIONS

Adger, B. et al., "The Synthesis of (R)-(+)-Lipoic Acid Using a Monooxygenase-Catalysed Biotransformation as the Key Step," *Bioorganic & Medicinal Chemistry*, vol. 5, No. 2, pp. 253-261, 1997.
d'Angelo, Jean et al., "A Short, Efficient, Highly Selective Synthesis of (1R,3S)-cis-Chrysanthemic Acid through the Microbiological Reduction of 2,2,5,5-Tetramethyl-1,4-cyclohexanedione," *J. Org. Chem.*, vol. 51, pp. 40-45, 1986.
Wipf, B. et al., "41. Production of (+)-(S)-Ethyl 3-Hydroxybutyrate and (−)-(R)-Ethyl 3-Hydroxybutyrate by Microbial Reduction of Ethyl Acetoacetate," *Helvetica Chimica Acta*, vol. 66, pp. 485-488, 1973.

Nakamura, K. et al., "Asymmetric Reduction of Ketones by Glycerol Dehydrogenase from Geotricum", *Tetrahedron Letters*, vol. 29, Nr. 20, 1988, pp. 2453-2454, XP001021318.
Database, Chemical Abstracts: R.N. Patel et al., "Stereoselective Reduction of Beta-keto Esters by Geotrichum Candidum", Database Accession No. 117:190226; XP002180887.
S. Servi: "Baker's Yeast as a Reagent in Organic Synthesis", Synthesis, Georg Thieme Verlag, Stuttgart, Germany, Bd. 93, 1990, Section 1-25, XP001018969.
J.S. Yadav et al., *J. Sci. Ind. Res.*, 1990, vol 49, pp. 400-409.
A.S. Gopalan et al., *Tetrahedron Letters*, 1989, pp. 5705-5708.

(Continued)

*Primary Examiner*—Irene Marx
(74) *Attorney, Agent, or Firm*—Buchanan Ingersoll & Rooney PC

(57) ABSTRACT

The invention relates to a process for the production of (R)- or (S)-8-chloro-6-hydroxyoctanoic acid alkyl esters of the general formula (R)-II or (S)-II,

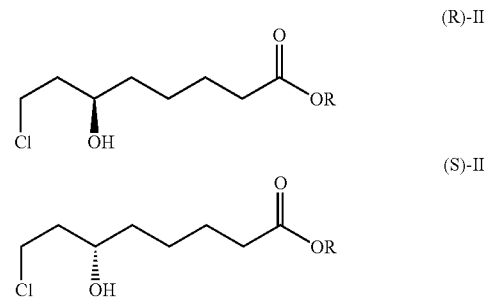

in which R means $C_{1-4}$ alkyl, from 8-chloro-6-oxo-octanoic acid alkyl esters of the general formula I,

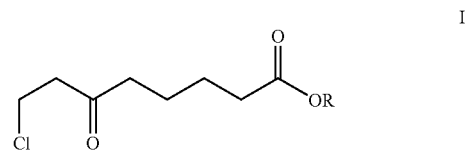

in which R has the above meaning.

The desired enantiomers are produced biocatalytically in an enantioselective reduction, wherein as desired the strains Mucor racemosus are used for (S)-II compounds and Geotrichum candidum for (R)-II compounds.

The resultant esters may, in known manner, be converted stereospecifically into (R)-α-lipoic acid.

2 Claims, No Drawings

OTHER PUBLICATIONS

L. Dasaradhi et al., *J. Chem. Commun.*, 1990, pp. 729-730.

Y.R. Santosh Laxmi and D.S. Iyengar, *Synthesis*, 1996, pp. 594-596.

M. Bezbaurau et al., *Synthesis*, 1996, pp. 1289-1290.

N.W. Fadnavis et al., *Tetrahedron: Asymmetry* 1997, vol. 8, No. 2, pp. 337-339.

N.W. Fadnavis et al., *Tetrahedron: Asymmetry* 1998, vol. 9, pp. 4109-4112.

S. Lee and Y. Ahn, *J. Korean Chem. Soc.*, 1999, vol. 43, pp. 128-130.

M.W. Bullock et al., *J. Am. Chem. Soc.*, 1954, vol. 76, pp. 1828-1832.

R.N. Patel et al., *Enzyme Microb. Technol.*, 1992, vol. 14, pp. 731-738.

PROCESS FOR THE ENANTIOSELECTIVE REDUCTION OF 8-CHLORO-6-OXO-OCTANOIC ACID ALKYL ESTERS

AREA OF USE OF THE IVENTION

The present invention relates to a novel biocatalytic process for the enantiose-lective reduction of prochiral 8-chloro-6-oxo-octanoic acid alkyl esters of the formula I as desired with the assistance of the strains Mucor racemosus or Geotrichum candidum to yield respectively the corresponding (S)- or (R)-enantiomer of the reaction products. Once the chiral centre has been formed, the further stereospecific conversion into R-α-lipoic acid may proceed in known manner (DE 195 33 881). As a racemate, α-lipoic acid is primarily used for treating diabetic neuropathy and acute and chronic liver disease. Since it is only the natural (R)-(+)-enantiomer which exhibits biological activity, asymmetric synthesis of this pure natural substance is of great importance.

CHARACTERISTICS OF THE KNOWN PRIOR ART

The compounds I are known and serve as intermediates for the large scale industrial production of racemic thioctic acid (M. W. Bullock et al., J. Am. Chem. Soc. 1954, 76, 1828).

The literature describes not only chemical synthesis processes but also processes comprising biocatalytic sub-stages for the production of enantiomerically pure (R)-α-lipoic acid (review article: J. S. Yadav et al., J. Sci. Ind. Res. 1990, 49, 400). Chemical, asymmetric synthesis processes generally require costly and complicated starting compounds since, for example, the possibility of using enantioselective chemocatalysis is associated with specific electronic and steric structural features.

Production processes with biocatalytic sub-stages use, on the one hand, en-zyme preparations of lipases and oxidoreductases and, on the other, yeast.

Known lipase-catalysed process stages (Y. R. Santosh Laxmi and D. S. Iyengar, Synthesis, 1996, 594; N. W, Fadnavis and K. Koteshwar, Tetrahedron: Asymmetry 1997, 8, 337; N. W. Fadnavis et al., Tetrahedron: Asymmetry 1998, 9, 4019; S. Lee and Y. Ahn, J. Korean Chem. Soc. 1999, 43, 128) are based on enantioselective ester cleavage in order to achieve elevated enantiomeric purity. These processes start from racemic mixtures. The biocatalytic reaction is only capable of utilising at most 50% of the racemic mixture to obtain the enantiomerically pure compound. The remaining unwanted enantiomer must either be discarded or be converted back into a racemic mixture by means of complex reaction stages. Processes with monooxygenases (B. Adger et al., Bioorg. Biomed. Chem. 1997, 5, 253) require costly cofactors, such as NADH or NADPH, or costly cofactor recycling systems.

It is known that yeast (Saccharomyces cerevisiae) and fungi of the genera Mucor and Geotrichum are capable of the biocatalytic conversion of intermediates.

Yeast has already long been used as a biocatalyst in reduction reactions of β-keto esters, ester cleavage and other syntheses (review article: S. Servi, Synthesis 1990, 93, 1).

Enantioselective ester cleavage reactions have in particular been described for Mucor species (for example Mucor miehei and Muco javanicus). While Mucor racemosus is only mentioned in relation to the reduction of tetramethyl-cyclo-hexanedione (J. d'Angelo et al. J. Org. Chem. 1986, 51, 40), the biocatalytic reduction of β-keto esters has been described for Geotrichum candidum (B. Wipf et al. Helv. Chim. Acta 1983, 66, 485).

No hitherto known processes with yeast (A. S. Gopalan and H. K. Hollie, Tetrahe-dron Lett. 1989, 30, 5705; L. Dasaradhi et al., J. Chem. Soc., 1990, 729; M. Bezbarua et al., Synthesis, 1996, 1289; DE 40 37 440) or Geotrichum candidum (B. Wipf et al. Helv. Chim. Acta 1983, 66, 485) are capable of enantioselectively converting intermediates with oxygen-free, small ligands in β-position relative to the reaction centre into the corresponding S- or R-enantiomers. Instead, large, oxygen-containing ligands are introduced by means of complicated intermediate stages into the β position relative to the keto group, which ligands then enable an enantioselective conversion.

In the solution described herein, in comparison with known syntheses, the starting compounds used are those which only bear very small ligands in α- or β-position to the keto group but are nevertheless converted with elevated enantioselectivity.

The solution presented here was particularly surprising relative to the known prior art since K. Nakamura et al. Tetrahedron Letters 29, 2453-4, 1988 describe that dehydrogenases recognise only ester functions and not chlorine atoms in the adjacent position to the reaction centre and give rise to enantiose-lective conversions.

DESCRIPTION OF THE ESSENCE OF THE INVENTION

The object underlying the invention was accordingly to provide, while making use of known synthesis building blocks, a simpler and more economic, biocatalytically-based process for asymmetric induction within the (R)-α-lipoic acid synthesis sequence.

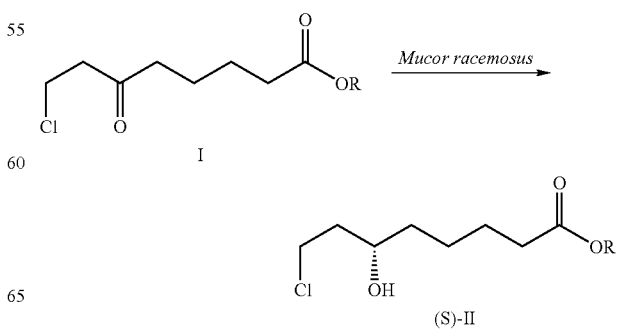

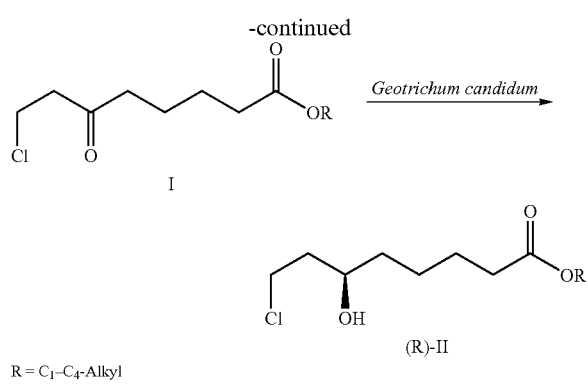

R = C$_1$–C$_4$-Alkyl

According to the invention, said object was achieved by finding novel processes which permit enantioselective reduction of the prochiral 8-chloro-6-oxo-octanoic acid alkyl esters of the formula I, in which R denotes C$_{1-4}$ alkyl, as desired with the assistance of the strains Mucor racemosus or Geotrichum candidum to yield respectively the corresponding (S)- or (R)-enantiomer. 8-Chloro-6-oxo-octanoic acid methyl ester has proved particularly suitable.

Enantioselective reduction of prochiral compounds to yield the (R)-enantiomer of the formula (R)-II proceeds with the assistance of Geotrichum candidum. Conversion of the prochiral precursors into the (S)-enantiomer of the formula (S)-II may be achieved by means of Mucor racemosus.

The elevated enantioselectivity of the reduction of 8-chloro-6-oxo-octanoic acid alkyl esters of the formula I was not to have been anticipated as elevated asymmetric induction has only been described in the literature for compounds in which sterically and/or electronically highly different groups promote selectivity on both sides in α- or β-position relative to the keto group. It was furthermore surprising that two strains could also be found which catalyse the conversion into opposite enantiomers at elevated yield and enantioselectivity.

The process according to the invention is distinguished from the prior art in that the 8-chloro-6-hydroxyoctanoic acid alkyl esters of the formula (R)-II are obtained by culturing Geotrichum candidum (DSM 13776; deposited Oct. 13, 2000 with the DSMZ-Deutsche Sammlung Von Mikroorganismen und Zellkulturen GmbH, Mascheroder Weg 1b, D-38124, Braunschweig, Germany) on a conventional fungal nutrient agar, preferably Sabouraud's glucose agar. The strain is precultured using a complex medium, preferably with 1% yeast extract, 2% peptone and 2% glucose. Further multiplication of biomass is achieved in a completely synthetic medium with glucose as carbon source, ammonium sulfate as nitrogen source together with further nutrient salts, preferably in the composition 20 g/l glucose, 3 g/l (NH$_4$)$_2$SO$_4$, 4 g/l KH$_2$PO$_4$, 0.5 g/l MgSO$_4$, 0.2 g/l NaCl, 0.2 g/l yeast extract, 3 mg/l FeCl$_3$×6 H$_2$O, 3 mg/l CaCl$_2$×2 H$_2$O, 0.4 mg/l MnSO$_4$×H$_2$O, 0.5 mg/l ZnSO$_4$× 7H$_2$O and 0.05 mg CuSO$_4$×5 H$_2$O. Both the preculture and the main culture are cultured at 19 to 28° C., preferably 24° C., over a period of 1 to 5 days, preferably 3 days, with shaking on an orbital shaker at 100 to 300 rpm, preferably 190 rpm.

The actual biocatalytic conversion is performed in a buffered aqueous solution with addition of glucose as energy source. The concentration of the biocatalyst is 0.1 to 100 g of biomass solids per litre, preferably 5 g of biomass solids per litre. The substrate is added to the biotransformation batch in a concentration of 5 g/l. Biotransformation is performed with shaking at 24° C. over 1 to 3 days.

Once the biotransformation is complete, the biomass is centrifuged off and the supernatant extracted twice with an organic solvent, preferably ethyl acetate. The extract obtained is evaporated to dryness. The crude product contains proportions of (R)-8-chloro-6-hydroxyoctanoic acid of the formula (R)-II (R=H), which are converted in known manner into the particular alkyl ester by subsequent esterification (DE 195 33 881).

Mucor racemosus (DSM 13775) is cultured and the conversions performed therewith in a similar manner to that described for Geotrichum candidum.

The crude product contains proportions of (S)-8-chloro-6-hydroxyoctanoic acid of the formula (S)-II (R=H), which are converted in known manner into the particular alkyl ester by subsequent esterification (DE 195 33 881).

The compounds (R)-II and (S)-II produced using the process according to the invention generally exhibit an elevated enantiomeric excess, corresponding to an optical yield of 70–95%. Enantiomer ratios are measured directly by chiral gas chromatography on optically active columns.

PRACTICAL EXAMPLES

Example 1

The strain Mucor racemosus (DSM 13775) is cultured on Sabouraud's agar at 24° C. 100 ml of YPD nutrient solution (1% yeast extract, 2% peptone and 2% glucose) is inoculated with an inoculating loop and incubated for 3 days at 24° C. on an orbital shaker (190 rpm). 10% of this preculture are transferred into 100 ml of SMG medium (20 g/l glucose, 3 g/l (NH$_4$)$_2$SO$_4$, 4 g/l KH$_2$PO$_4$, 0.5 g/l MgSO$_4$, 0.2 g/l NaCl, 0.2 g/l yeast extract, 3 mg/l FeCl$_3$×6 H$_2$O, 3 mg/l CaCl$_2$×2 H$_2$O, 0.4 mg/l MnSO$_4$×H$_2$O, 0.5 mg/l ZnSO$_4$×7 H$_2$O and 0.05 mg CuSO$_4$×5 H$_2$O) and cultured for a further 3 days at 24° C.

The resultant biomass is centrifuged off and transferred into 100 ml of buffered aqueous solution (50 mmol Na phosphate buffer, pH 6.5) comprising 5 g/l of glucose. 0.5 g of 8-chloro-6-oxo-octanoic acid methyl ester are dissolved in 2 ml of ethanol and added to the biotransformation batch. After 24 hours, the biomass is removed and the medium extracted twice with 50 ml portions of ethyl acetate. The extracts are combined and the solvent stripped out in a rotary evaporator. The residue is redissolved with 10 ml of methanol and, after addition of 0.04 ml of conc. HCl, refluxed for 1 hour. The solvent is then removed by distillation. Once the residue has been purified by column chromatography (silica gel, ethyl acetate:hexane=3:1), 0.33 g (66%) of (S)-8-chloro-6-hydroxyoctanoic acid methyl ester are obtained with an enantiomeric excess of 92% (chiral GC).

Example 2

The strain Geotrichum candidum (DSM 13776) is cultured on Sabouraud's agar at 24° C. 100 ml of YPD nutrient solution (1% yeast extract, 2% peptone and 2% glucose) is inoculated with an inoculating loop and incubated for 3 days at 24° C. on an orbital shaker (190 rpm). 10% of this preculture are transferred into 100 ml of SMG medium (20 g/l glucose, 3 g/l $(NH_4)_2SO_4$, 4 g/l $KH_2PO_4$, 0.5 g/l $MgSO_4$, 0.2 g/l NaCl, 0.2 g/l yeast extract, 3 mg/l $FeCl_3 \times 6\ H_2O$, 3 mg/l $CaCl_2 \times 2\ H_2O$, 0.4 mg/l $MnSO_4 \times H_2O$, 0.5 mg/l $ZnSO_4 \times 7\ H_2O$ and 0.05 mg $CuSO_4 \times 5\ H_2O$) and cultured for a further 3 days at 24° C.

The resultant biomass is centrifuged off and transferred into 100 ml of buffered aqueous solution (50 mmol Na phosphate buffer, pH 6.5) comprising 5 g/l of glucose. 0.5 g of 8-chloro-6-oxo-octanoic acid methyl ester are dissolved in 2 ml of ethanol and added to the biotransformation batch. After 24 hours, the biomass is removed and the medium extracted twice with 50 ml portions of ethyl acetate. The extracts are combined and the solvent stripped out in a rotary evaporator. The residue is redissolved with 10 ml of methanol and, after addition of 0.04 ml of conc. HCl, refluxed for 1 hour. The solvent is then removed by distillation. Once the residue has been purified by column chromatography (silica gel, ethyl acetate:hexane=3:1), 0.31 g (62%) of (R)-8-chloro-6-hydroxyoctanoic acid methyl ester are obtained with an enantiomeric excess of 88% (chiral GC).

What is claimed is:

1. A process for the production of (R)-8-chloro-6-hydroxyoctanoic acid alkyl esters of the formula (R)-ll from 8-chloro-6-oxo-octanoic acid alkyl esters of the formula I,

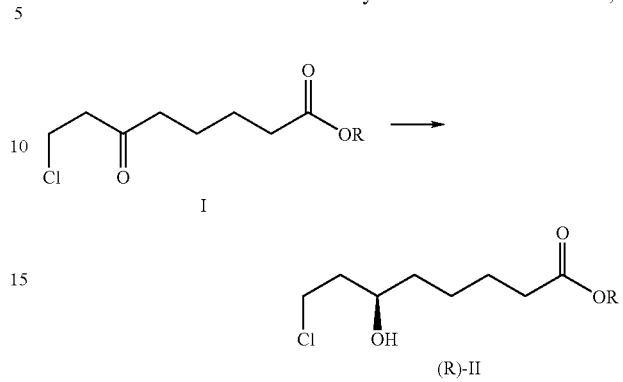

in which P. in each case means C alkyl, wherein the reaction is performed by means of a biocatalyst, wherein the biocatalyst is *Geotrichum candidum* of the strain DSM 13776; and wherein the (R)-8-chloro-6-hydroxyoctanoic acid alkyl esters of the formula (R)-ll are isolated and recovered.

2. A process according to claim 1, wherein 8-chloro-6-oxo-octanoic acid methyl ester is used as the prochiral starting compound.

* * * * *